US011007032B2

(12) United States Patent
Gupta (10) Patent No.: US 11,007,032 B2
(45) Date of Patent: May 18, 2021

(54) ENDOSCOPE CLEANING DEVICE (71) Applicant: Cedars-Sinai Medical Center, Los Angeles, CA (US)

(72) Inventor: Kapil Gupta, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 198 days.

(21) Appl. No.: 15/570,545

(22) PCT Filed: May 11, 2016

(86) PCT No.: PCT/US2016/031744
§ 371 (c)(1),
(2) Date: Oct. 30, 2017

(87) PCT Pub. No.: WO2016/183136
PCT Pub. Date: Nov. 17, 2016

(65) Prior Publication Data
US 2018/0147022 A1 May 31, 2018

Related U.S. Application Data (60) Provisional application No. 62/160,438, filed on May 12, 2015.

(51) Int. Cl.
*A61B 90/70* (2016.01)
*A61B 1/12* (2006.01)
(Continued)

(52) U.S. Cl.
CPC .............. *A61B 90/70* (2016.02); *A61B 1/122* (2013.01); *A61B 1/00137* (2013.01);
(Continued)

(58) Field of Classification Search
None
See application file for complete search history.

(56) References Cited

U.S. PATENT DOCUMENTS 4,288,882 A 9/1981 Takeuchi
5,090,433 A * 2/1992 Kamaga ................. A61B 1/122
134/169 C
(Continued)

FOREIGN PATENT DOCUMENTS

CN 1649630 A 8/2005
CN 101513341 A 8/2009
(Continued)

OTHER PUBLICATIONS

JPH03280925 English Translation, accessed on Sep. 2020. (Year: 1991).*
(Continued)

*Primary Examiner* — Eric W Golightly
*Assistant Examiner* — Arlyn I Rivera-Cordero
(74) *Attorney, Agent, or Firm* — Nixon Peabody LLP (57) ABSTRACT The invention relates to devices, systems and methods for cleaning medical tools having an elevator mechanism; for example, duodenoscopes, linear echoendoscopes, and side viewing endoscopes. The device includes two nozzles for being positioned near and/or inserted in spaces around the elevator mechanism. The system includes the device and a pump to supply liquid to the device.

19 Claims, 10 Drawing Sheets

(51) Int. Cl.
*A61B 90/00* (2016.01)
*A61B 1/00* (2006.01)
*A61L 2/18* (2006.01)

(52) U.S. Cl.
CPC ......... *A61B 2090/701* (2016.02); *A61L 2/18* (2013.01); *A61L 2202/24* (2013.01)

(56) References Cited

U.S. PATENT DOCUMENTS

| | | | | |
|---|---|---|---|---|
| 5,193,561 | A * | 3/1993 | Robb | B08B 3/02 134/102.1 |
| 5,279,317 | A * | 1/1994 | Bowman | A61B 1/121 134/166 C |
| 5,558,841 | A | 9/1996 | Nakagawa | |
| 6,558,620 | B1 | 5/2003 | Sanford et al. | |
| 6,582,654 | B1 * | 6/2003 | Kral | A61B 1/123 134/161 |
| 6,797,681 | B2 | 9/2004 | Fricker et al. | |
| 9,278,149 | B2 | 3/2016 | Suzuki et al. | |
| 2005/0065405 | A1 | 3/2005 | Hasegawa | |
| 2008/0277352 | A1 * | 11/2008 | White | C02F 1/481 210/695 |
| 2013/0098407 | A1 * | 4/2013 | Perlman | A61B 90/70 134/36 |
| 2014/0134071 | A1 | 5/2014 | Suzuki et al. | |

FOREIGN PATENT DOCUMENTS

| | | | |
|---|---|---|---|
| CN | 107530458 | A | 1/2018 |
| EP | 1938743 | A1 | 7/2008 |
| EP | 3294346 | | 3/2018 |
| JP | 03-280925 | H | 12/1991 |
| JP | H05228113 | A | 9/1993 |
| JP | 06-98857 | H | 4/1994 |
| JP | 08-196505 | H | 8/1996 |
| JP | 2018519877 | A | 7/2018 |
| WO | 2007000039 | A1 | 1/2007 |
| WO | 2016/183136 | A1 | 11/2016 |

OTHER PUBLICATIONS

International Search Report and Written Opinion for PCT/US2016/031744, dated Aug. 4, 2016, 8 pages.
Arc Healthcare Solutions, ECS1 Endoscope Cleaning Station, Retrieved from Internet: <http://www.arc-hcs.com/endoscope-cleaning-station-ecs1.html/>, 2015, 11 pages.
Hydrofloss, Hydro Floss: The New Generation of Oral Irrigator, Retrieved from Internet: <http://hydrofloss.com/products/hydrofloss.php5/>, 2015, 2 pages.
Custom Ultrasonics, Inc., Summary and Overview Safety, Efficacy and Microbiological Considerations System 83 Plus Washer-Disinfector, 2007, MKT-0001, Rev. B (internet version), 26 pages.
endonurse.com, Developments in ERCP, 2008, 3 pages.
Johnson et al., The Effectiveness of a Magnetized Water Oral Irrigator (Hydro Floss) on Plaque, Calculus and Gingival Health, J. Clin. Periodontol, 1998, vol. 25, pp. 316-321.
Watt et al., The Effect of Oral Irrigation with a Magnetic Water Treatment Device on Plaque and Calculus, J. Clin. Periodontol, 1993, vol. 20, pp. 314-317.
Watt et al., The Effect of Oral Irrigation with a Magnetic Water Treatment Device on Plaque and Calculus (Condensed Version), J. Clin. Periodontol, 1993, vol. 20, pp. 314-317.
International Preliminary Report on Patentability for PCT/US2016/031744, dated Nov. 14, 2017, 5 pages.
Extended European Search Report of EP 16793401.7, dated Dec. 13, 2018, 8 Pages.

* cited by examiner

ENDOSCOPE CLEANING DEVICE

CROSS-REFERENCE TO RELATED APPLICATIONS

This application is a National Phase of International Application No. PCT/US2016/031744 filed May 11, 2016, currently pending, which designated the U.S. and that International Application was published under PCT Article 21(2) in English, which also includes a claim of priority under 35 U.S.C. § 119(e) to U.S. provisional patent application No. 62/160,438 filed May 12, 2015, the entirety of which is hereby incorporated by reference.

FIELD OF THE INVENTION

The invention relates to a device and method for cleaning tools including but not limited to duodenoscopes, linear echoendoscopes, side viewing endoscopes, other endoscopes and medical tools with an elevator mechanism, and medical tools with any part or system where standard cleaning with available brushes is not possible.

BACKGROUND

It is challenging to appropriately clean side viewing duodenoscopes and linear echoendoscopes, other endoscopes and medical tools with an elevator mechanism, and medical tools with any part or system where standard cleaning with available brushes is not possible. The limitation is because of narrow crevices and spaces surrounding the elevator, which cannot be manually reached and cleaned appropriately. The retained debris and body fluids have been reported to be the reason for transmission of multi-drug resistant bacteria. Therefore, there is a need for devices and systems for cleaning medical tools having an elevator mechanism or difficult-to-reach crevices and spaces, including but not limited to duodenoscopes, linear echoendoscopes, and other side viewing endoscopes.

SUMMARY OF THE INVENTION

The following embodiments and aspects thereof are described and illustrated in conjunction with systems, compositions and methods which are meant to be exemplary and illustrative, not limiting in scope.

Various embodiments of the present invention provide a device for cleaning a tool comprising an elevator. The device may comprise: a container comprising two nozzles, one, two, three, four, five or more tubes, and drainage holes in the bottom of the container, wherein the two nozzles are fluidly connected to the one, two, three, four, five or more tubes, and wherein the two nozzles are configured for being positioned near and/or inserted into the spaces around the elevator; and a cover, wherein when the cover is closed onto the container, the cover and the container form water tight seal along the edges where the cover contacts the container and one opening comprising a water seal rim, and wherein the opening is configured for holding the tool and the water seal rim is configured for forming water tight seal around the tool. Various embodiments of the present invention also provide a combination of a device as described herein and a tool comprising an elevator.

Various embodiments of the present invention provide a system for cleaning a tool comprising an elevator. The system may comprise: a device, comprising: a container comprising two nozzles, one, two, three, four, five or more tubes, and drainage holes in the bottom of the container, wherein the two nozzles are fluidly connected to the one, two, three, four, five or more tubes, and wherein the two nozzles are configured for being positioned near and/or inserted into the spaces around the elevator of the tool; and a cover, wherein when the cover is closed onto the container, the cover and the container form water tight seal along the edges where the cover contacts the container and one opening comprising a water seal rim, and wherein the opening is configured for holding the tool and the water seal rim is configured for forming water tight seal around the tool; and a pump configured for supplying a liquid into the device, wherein the pump is connected to the device through the one, two, three, four, five or more tubes. Various embodiments of the present invention also provide a combination of a system as described herein and a tool comprising an elevator.

In various embodiments, the system may further comprise a magnetic water generator configured for magnetically charging the liquid, wherein the magnetic water generator is connected to the pump through the one, two, three, four, five or more tubes. In various embodiments, the system may further comprise a vacuum configured for removing air and/or liquid out of the device, wherein the vacuum is connected to the device through the one, two, three, four, five or more tubes. In various embodiments, the system may further comprise a drainage collection component, wherein the drainage collection component is configured for receiving the bottom of the device and collecting the liquid drained through the drainage holes. In some embodiments, the drainage collection component and the bottom of the device may be configured for forming air tight seal along the edges where the drainage collection component contacts the bottom of the device. In various embodiments, the system may further comprise a vacuum connected to the drainage collection component and configured for removing air and/or liquid out of the drainage collection component. In various embodiments, the system may further comprise a medical tool comprising an elevator.

Various embodiments of the present invention provide a method of cleaning a medical tool comprising an elevator. The method may comprise: inserting the medical tool into a device or system as described herein; and actuating the device or system to clean the medical tool. In accordance with the present invention, the tool may be a duodenoscope, a linear echoendoscopes, or a side viewing endoscope.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

One embodiment of the present invention is a disposable, single use, enclosed device with two internal nozzles. Another embodiment of the present invention is a reusable enclosed device with two internal nozzles. The nozzles are placed in such a way that they enter into the two spaces around the elevator. The tip of the endoscope rests in a tray and the top of the device is closed creating a closed, water proof chamber. The nozzles are in turn connected to a pump and/or apparatus which magnetically charge the water and pump the magnetic water with a high physical force as a forced jet. Water can be changed to a disinfectant solution or yet another solution, or the water, disinfectant solution and/or other solution can be alternated. The force of the water and the magnetic charge clear debris and fluid which may be otherwise hard to reach. Further, the same system can be used with an antiseptic solution to clean the scope after the magnetic hydrostatic cleaning. This cleaning process using the magnetic water can be done right after the procedure or even before a procedure whereby every scope is cleaned again just before each use. Advantages of the device include: magnetically charged water prevents bacteria from sticking to the surface; high pressure water jet removes debris and body fluids from deep crevices which are otherwise hard to clean; and the ability to use different fluids like disinfectant fluids can reduce or eliminate chances of transmission of infection.

Various embodiments of the present invention provide devices, systems and methods for cleaning medical tools with an elevator mechanism, including but not limited to duodenoscopes, linear echoendoscopes, side viewing endoscopes, and medical tools that have difficult-to-reach areas, spaces or crevices and require manual cleaning. In accordance with the present invention, an "elevator" mechanism refers to a movable mechanism that changes the angle of an accessory exiting an accessory channel of a medical tool. For example, the elevator mechanism of duodenoscopes allows duodenoscopes to access the ducts to treat problems with fluid drainage. One step of the manual cleaning is to brush the elevator area. However, the moving parts of the elevator mechanism contain microscopic crevices that may not be reached with a brush. Residual body fluids and organic debris may remain in these crevices after cleaning and disinfection. If these fluids contain microbial contamination, subsequent patients may be exposed to serious infections.

In various embodiments, the present invention provides a device for cleaning a tool comprising an elevator. In various embodiments, the device comprises two nozzles and one or more tubes. In some embodiments, the device comprises two nozzles and two, three, four or five tubes. The two nozzles are fluidly connected to the one, two, three, four, five or more tubes, and are configured for being positioned near and/or inserted into the spaces around the elevator. In some embodiments, the device further comprises a handle configured for being held by hands. In various embodiments, one may hold the device, and position the two nozzles near or insert the two nozzles into the spaces around the elevator. In some embodiments, the device comprises one tube fluidly connected to the two nozzles. In other embodiments, the device comprises two tubes fluidly connected to the two nozzles.

In various embodiments, the present invention provides a system for cleaning a tool comprising an elevator. The system comprises a device and a pump configured for supplying a liquid into the device. In various embodiments, the device comprises two nozzles and one or more tubes. In some embodiments, the device comprises two nozzles and two, three, four or five tubes. The two nozzles are fluidly connected to the one, two, three, four, five or more tubes, and are configured for being positioned near and/or inserted into the spaces around the elevator. The pump is connected to the device through the one, two, three, four, five or more tubes. In some embodiments, the device further comprises a handle configured for being held by hands. In various embodiments, one may hold the device, and position the two nozzles near or insert the two nozzles into the spaces around the elevator. In some embodiments, the device comprises one tube fluidly connected to the two nozzles. In other embodiments, the device comprises two tubes fluidly connected to the two nozzles.

In various embodiments, the present invention provides a device for cleaning a tool comprising an elevator. The device comprises a container and cover. In various embodiments, the container comprises two nozzles; one or more tubes; and drainage holes in the bottom of the container. In some embodiments, the container comprises two nozzles; two, three, four or five tubes; and drainage holes in the bottom of the container. The two nozzles are fluidly connected to the one, two, three, four, five or more tubes, and are configured for being positioned near and/or inserted into the spaces around the elevator. When the cover is closed onto the container, the cover and the container may form a water tight seal along the edges where they contact each other and may form one opening comprising a water seal rim. The opening is configured for holding the tool and the water seal rim is configured for forming a water tight seal around the tool. In some embodiments, the device comprises one tube fluidly connected to the two nozzles. In other embodiments, the device comprises two tubes fluidly connected to the two nozzles.

In various embodiments, the present invention provides a system for cleaning a tool comprising an elevator. The system comprises a device and a pump configured for supplying a liquid into the device. The device comprises a container and cover. The container comprises two nozzles; one or more tubes; and drainage holes in the bottom of the container. In some embodiments, the container comprises two nozzles; two, three, four or five more tubes; and drainage holes in the bottom of the container. The two nozzles are fluidly connected to the one, two, three, four, five or more tubes, and are configured for being positioned near and/or inserted into the spaces around the elevator. The pump is connected to the device through the one, two, three, four, five or more tubes. When the cover is closed onto the container, the cover and the container may form a water tight seal along the edges where they contact each other and may form one opening comprising a water seal rim. The opening is configured for holding the tool and the water seal rim is configured for forming a water tight seal around the tool. In some embodiments, the device comprises one tube fluidly connected to the two nozzles. In other embodiments, the device comprises two tubes fluidly connected to the two nozzles.

In accordance with the present invention, a water tight seal can be implemented with a gasket made of rubber, nitrile rubber, silicone, neoprene, urethane, polytetrafluoroethylene (PTFE or Teflon), polychlorotrifluoroethylene, or ethylene propylene diene monomer (EPDM), or their combinations. In accordance with the present invention, the water seal rim can be made of rubber, nitrile rubber, silicone, neoprene, urethane, polytetrafluoroethylene (PTFE or Teflon), polychlorotrifluoroethylene, or ethylene propylene diene monomer (EPDM), or their combinations. In various embodiments, the opening configured for holding the tool can be of various shapes, including but not limited to circle, ellipse, oval, triangle, rectangle, square, rhombus, pentagon, hexagon, heptagon, octagon, nonagon, decagon, and polygon, and their combinations.

In one embodiment, the tool is a duodenoscope. In another embodiment, the tool is a linear echoendoscope. In still another embodiment, the tool is a side viewing endoscope. In various embodiments, the tool is an endoscope or medical tool that has difficult-to-reach areas, spaces or crevices and requires manual cleaning.

In various embodiments, the liquid is water, magnetically charged water, a water-based solution, or a magnetically charged water-based solution. In various embodiments, the liquid is a disinfectant solution.

In various embodiments, the pump is a high pressure pump. In some embodiments, the pump is configured for pressurizing the liquid to about 40-60, 60-80, 80-100, 100-120, 120-140, 140-160, 160-180, or 180-200 PSI. In various embodiments, the system further comprises a magnetic water generator configured for magnetically charging the liquid, wherein the magnetic water generator is connected to the pump through the one, two, three, four, five or more tubes.

In various embodiments, the system further comprises a vacuum configured for removing air and/or liquid out of the device, wherein the vacuum is connected to the device through the one, two, three, four, five or more tubes.

In various embodiments, the system further comprises a drainage collection component, wherein the drainage collection component is configured for receiving the bottom of the device and collecting the liquid drained through the drainage holes. In some embodiments, the drainage collection component and the bottom of the device are configured for forming air tight seal along the edges where the drainage collection component contacts the bottom of the device. In accordance with the present invention, air tight seal can be implemented with a gasket made of rubber, nitrile rubber, silicone, neoprene, urethane, polytetrafluoroethylene (PTFE or Teflon), polychlorotrifluoroethylene, or ethylene propylene diene monomer (EPDM), or their combinations. In some embodiments, the system further comprises a vacuum connected to the drainage collection component and configured for removing air and/or liquid out of the drainage collection component.

Various embodiments of the present invention provide a combination of a device described herein and a medical tool comprising an elevator. In one embodiment, the device may be used to clean the medical tool. In one embodiment, the tool is a duodenoscope. In another embodiment, the tool is a linear echoendoscope. In still another embodiment, the tool is a side viewing endoscope. In various embodiments, the tool is an endoscope or medical tool that has difficult-to-reach areas, spaces or crevices and requires manual cleaning.

Various embodiments of the present invention provide a method of cleaning a medical tool comprising an elevator. The method comprises inserting the medical tool into a device described herein; and actuating the device to clean the medical tool.

Various embodiments of the present invention provide a method of cleaning a medical tool comprising an elevator. The method comprises providing a high pressure liquid jet and using the high pressure liquid jet to clean the medical tool. In various embodiments, the high pressure liquid jet is directed near or into the spaces around the elevator. In various embodiments, the high pressure liquid jet is provided by a device described herein. In various embodiments, the liquid of the high pressure liquid jet is water, magnetically charged water, a water-based solution, or a magnetically charged water-based solution. In various embodiments, the liquid of the high pressure liquid jet is a disinfectant solution.

In various embodiments, a cleaning device as described herein is transparent so that one can monitor the cleaning process. In various embodiments, some parts of a cleaning system as described herein (for example, the top cover, bottom container and drainage collection component) can be disposable, and other parts (for example, the solution reservoir, magnetic water generator and water pump) are reusable. In various embodiments, some parts of a cleaning system as described herein (for example, the top cover, bottom container and drainage collection component) are manufactured as one unit through single injection molding. In some embodiments, the top cover and bottom container are connected through a winding hinge or a mechanical hinge. In some embodiments, the top cover and bottom container have a snap fit style latch.

FIGS. 1-5 illustrate one non-limiting example of the present invention. The cleaning device comprises a top cover 1 and a bottom container 2. The top cover and the bottom container can close onto each other to optionally form a water tight seal along their edges, and may include one opening 3 shown on the right side. The opening 3 may comprise a water seal rim 4 along its periphery.

Figure 1:
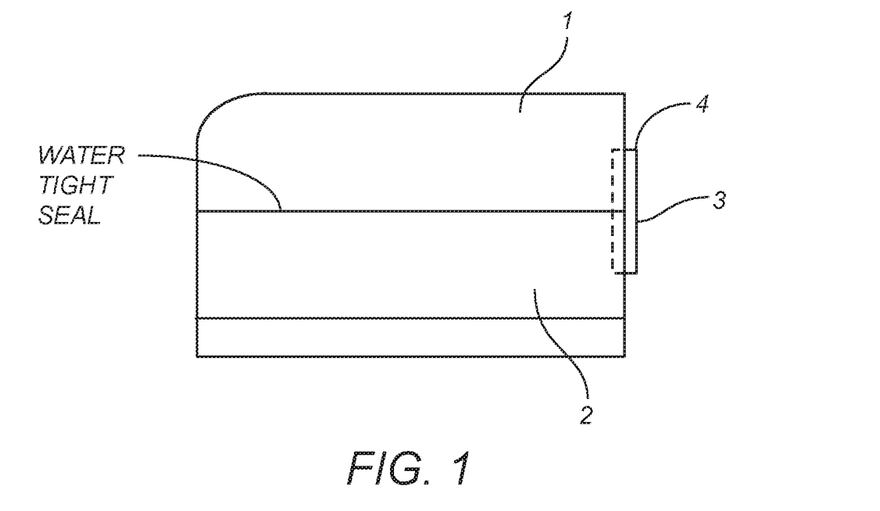
FIG. 1 illustrates, in accordance with various embodiments of the present invention, one non-limiting example of cleaning devices described herein.
Figure 2:
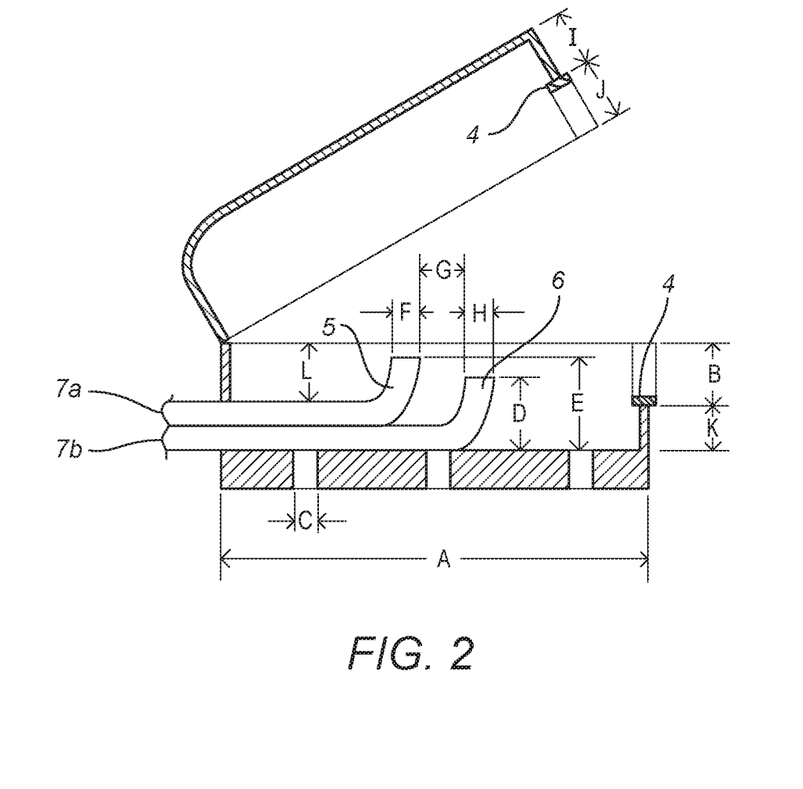
FIG. 2 illustrates, in accordance with various embodiments of the present invention, further views of the non-limiting example shown in FIG. 1. The top cover is opened.
Figure 3:
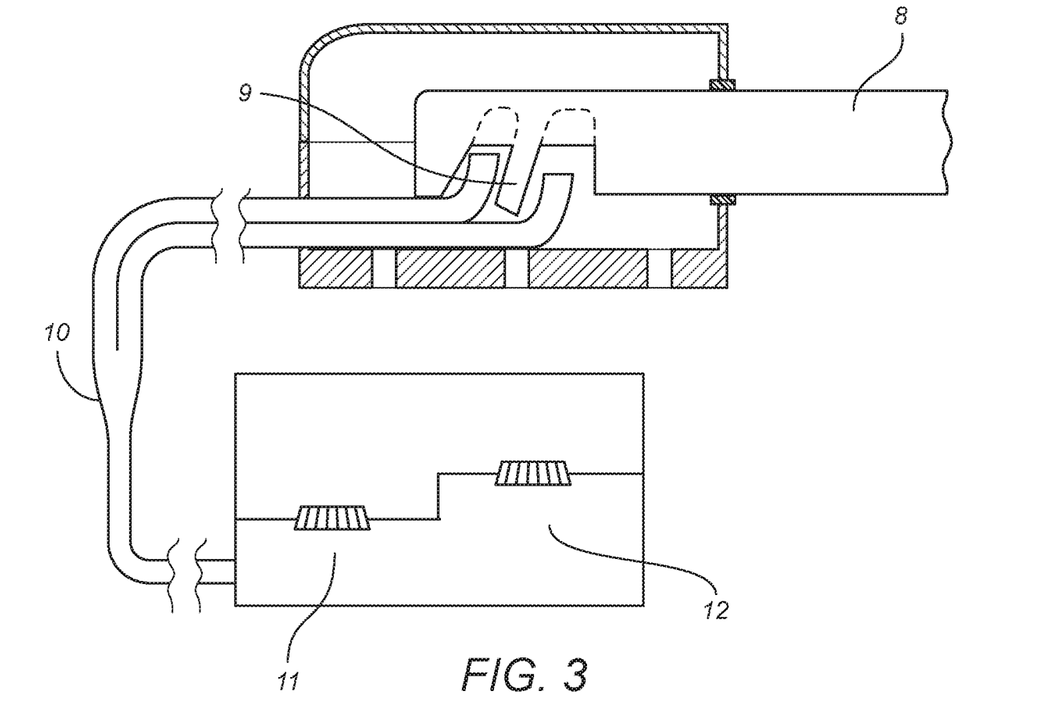
FIG. 3 illustrates, in accordance with various embodiments of the present invention, further views of the non-limiting example shown in FIG. 1. An endoscope is being cleaned.
Figure 4:
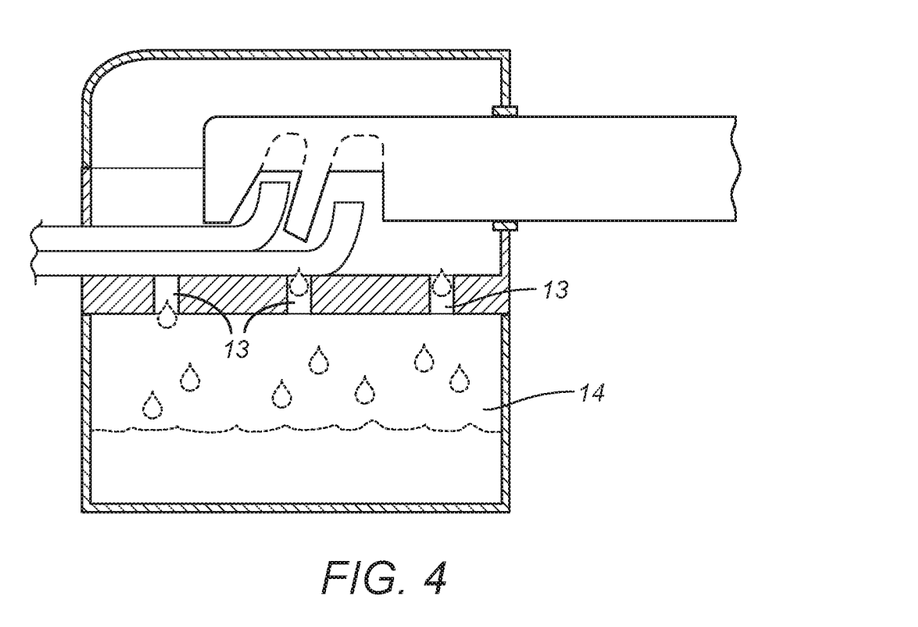
FIG. 4 illustrates, in accordance with various embodiments of the present invention, further views of the non-limiting example shown in FIG. 1.
Figure 5:
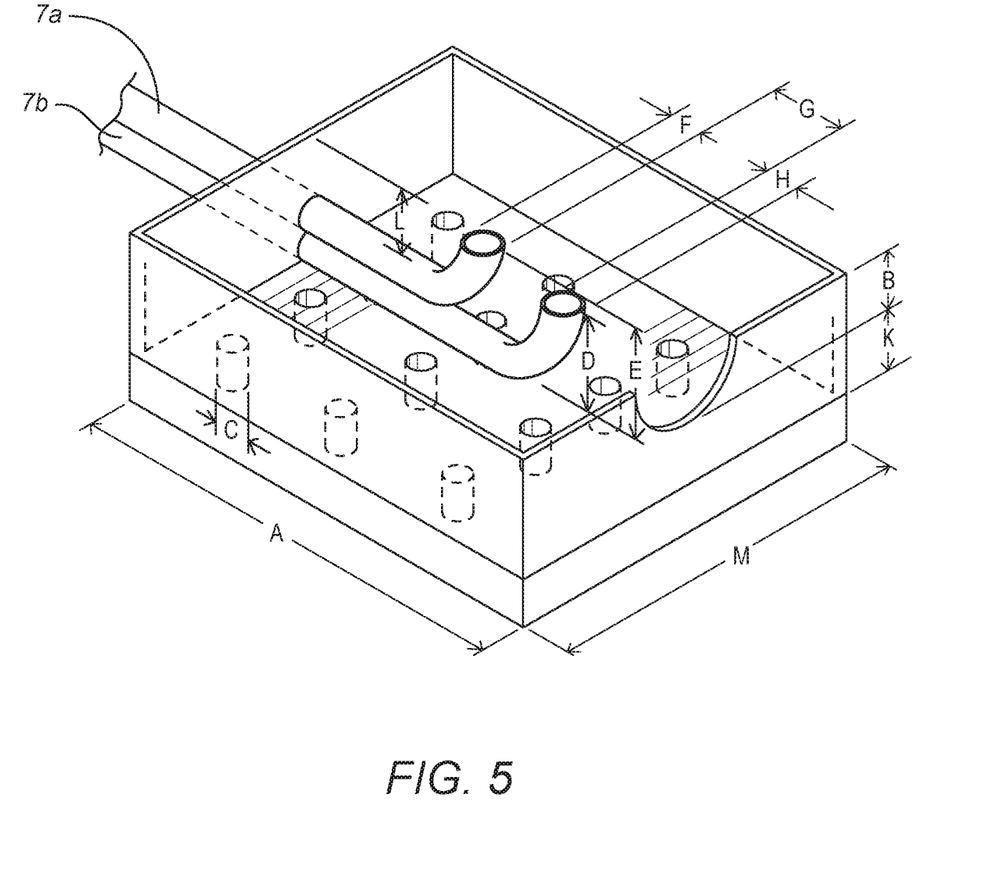
FIG. 5 illustrates, in accordance with various embodiments of the present invention, a three-dimensional view of the bottom container of the non-limiting example shown in FIG. 1. In this non-limiting example, the two nozzles 5 and 6 are connected to two separate tubes 7a and 7b.

The bottom container comprises nozzle 5 and nozzle 6, which are in fluid communication with tubes 7a and 7b. The two nozzles 5 and 6 are configured to match or otherwise accommodate the space geometry surrounding an elevator of endoscopes (e.g., duodenoscopes, linear echoendoscopes, side viewing endoscopes, and other endoscopes with an elevator mechanism). As a result, the two nozzles 5 and 6 can be positioned close to and/or inserted, to independently varying angles and/or depths, into the recesses surrounding the elevator. FIG. 5 provides a three-dimensional view of the bottom container of the non-limiting example.

The measurements of this non-limiting example are in the following approximate ranges: A is about 50-70 mm; B is about 6 mm; C is about 4-5 mm; D is about 7 mm; E is about 10 mm; F is about 2-2.5 mm, G is 12-15 mm; H is about 2-2.5 mm; I is about 10 mm; J is about 6 mm; K is about 10 mm; L is about 10 mm; and M is about 30-40 mm. Further these dimensions can be modified depending on the internal architecture of the endoscopes, duodenoscopes, or linear echoendoscopes for which the specific device is made. The devices and systems described herein can be used to clean any medical tools with an elevator mechanism, including but not limited to duodenoscopes, linear echoendoscopes, and other endoscopes, such as those endoscopes manufactured by OLYMPUS, PENTAX, FUJIFILM and other manufacturers. One of ordinary skill in the art would understand how to modify the measurements to match or otherwise accommodate the space geometry surrounding the elevator of these medical tools, so that the two nozzles can be positioned close to and/or inserted, to independently varying angles and/or depths, into the recesses surrounding the elevator in such tools.

For cleaning an endoscope tip 8 with an elevator 9 (for example, the tip of a duodenoscope), the endoscope tip 8 is placed into the bottom container, and the two nozzles 5 and 6 are inserted into the recesses surrounding the elevator 9. The top cover 1 is closed onto the bottom container 2. A water tight seal is formed along the edges where the top cover 1 and the bottom container 2 contact each other. The opening 3 encloses the endoscope tip 8 and the water seal rim 4 forms water tight seal around the endoscope tip 8. The tubes 7a and 7b are connected via one or more connecting tubes 10 to various components of the endoscope cleaning system described herein, which may include, but are not limited to, a water pump 11 for supplying high pressure water or solution jets into the endoscope cleaning device; a magnetic water generator 12 for magnetically charging water or other solutions, including but not limited to solutions like anti-infection solutions, anti-septic solutions, foam forming soap solutions, and other disinfectants, supplied into the endoscope cleaning device; an air pump for supplying high pressure air into the endoscope cleaning device; and a vacuum for removing air, water, or other solutions out of the endoscope cleaning device.

The endoscope cleaning device can also comprise drainage holes 13 on the bottom of the bottom container 2. A drainage collection component 14 can be placed under the endoscope cleaning device for collecting the liquid and debris drained from the endoscope cleaning device. The drainage collection component 14 and the bottom container 2 of the endoscope cleaning device can form water and/or air tight seals along the edges where they contact each other. The drainage collection component 14 can be connected to a vacuum for removal of the liquid and debris drained from the endoscope cleaning device.

Figure 6:
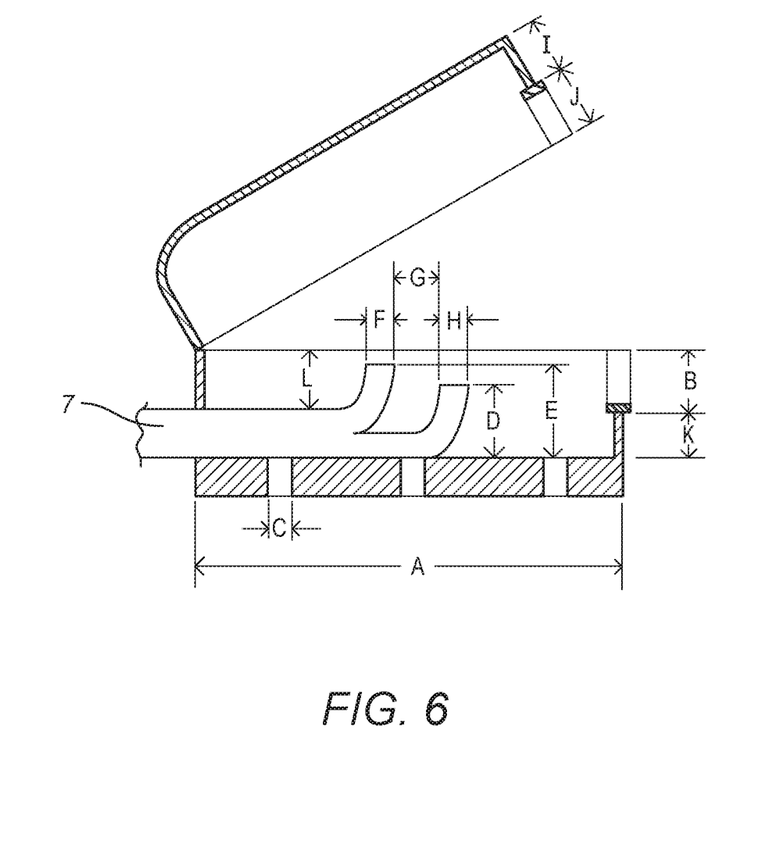
FIG. 6 illustrates, in accordance with various embodiments of the present invention, another non-limiting example of endoscope cleaning devices described herein. In this non-limiting example, the two nozzles 5 and 6 are connected to one tube 7.

The two nozzles 5 and 6 can be connected to two separate tubes 7a and 7b (FIG. 1-5) or one tube 7 (FIG. 6). The measurements of these non-limiting examples are in the ranges as follows: A is about 50-70 mm; B is about 6 mm; C is about 4-5 mm; D is about 7 mm; E is about 10 mm; F is about 2-2.5 mm, G is 12-15 mm; H is about 2-2.5 mm; I is about 10 mm; J is about 6 mm; K is about 10 mm; L is about 10 mm; and M is about 30-40 mm.

Figure 7A:
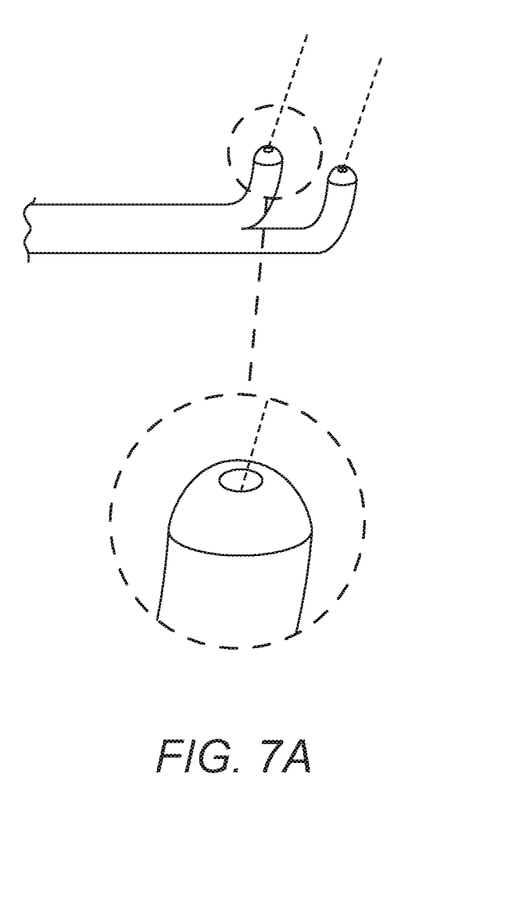
FIG. 7A and FIG. 7B illustrate, in accordance with various embodiments of the present invention, that the tips of the two nozzles 5 and 6 can be configured for various spray patterns, including but not limited to a single jet (FIG. 7A) and multiple jets (FIG. 7B). The spray patterns for the multiple jets may be independently selected to have the same or different spray patterns.
Figure 7B:
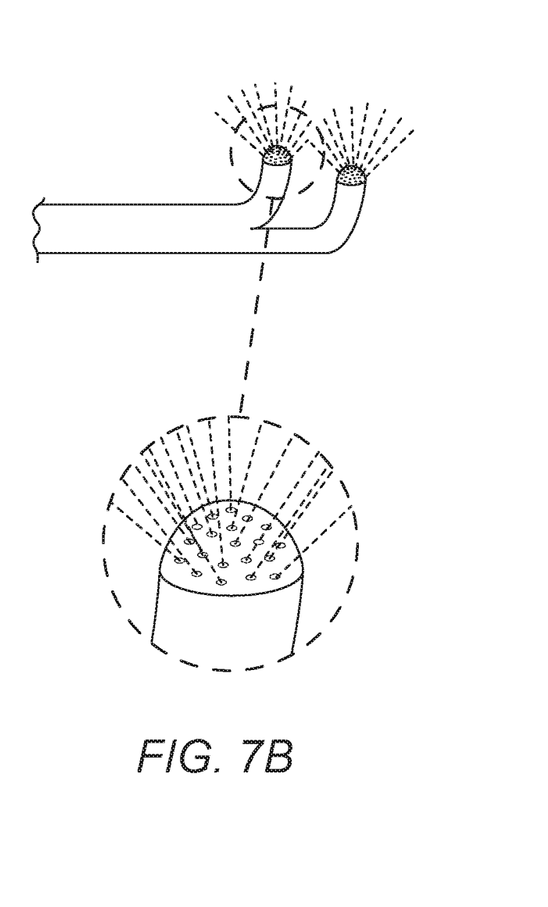

The tips of the two nozzles 5 and 6 can be configured for various spray patterns, including but not limited to a single jet (FIG. 7A) and multiple jets (FIG. 7B). The spray patterns for the multiple jets may be independently selected to have the same or different spray patterns.

Figure 9:
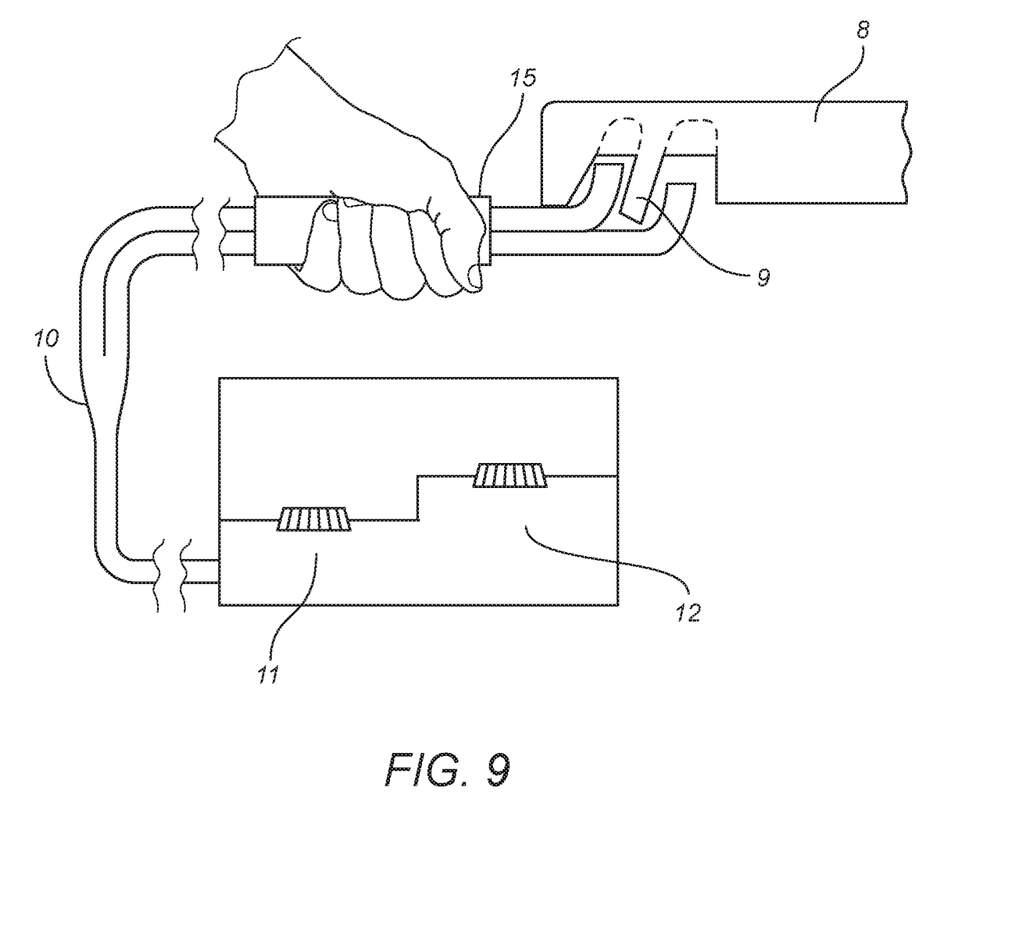
FIG. 9 illustrates, in accordance with various embodiments of the present invention, one non-limiting example of cleaning devices described herein. This non-limiting example is a hand-held device.

In various embodiments, a cleaning devices described herein can be a hand-held device, one non-limiting example of which is shown in FIG. 9. The tip 8 of an endoscope (for example, a duodenoscope) has an elevator 9. One holds the handle 15, and inserts the two nozzles into the recesses surrounding the elevator 9. The two nozzles are connected via one or more connecting tubes 10 to various components of the endoscope cleaning system described herein, which may include, but are not limited to, a water pump 11 for supplying high pressure water or solution jets into the endoscope cleaning device; a magnetic water generator 12 for magnetically charging water or other solutions, including but not limited to solutions like anti-infection solutions, anti-septic solutions, foam forming soap solutions, and other disinfectants, supplied into the endoscope cleaning device; an air pump for supplying high pressure air into the endoscope cleaning device; and a vacuum for removing air, water, or other solutions out of the endoscope cleaning device.

Figure 10A:
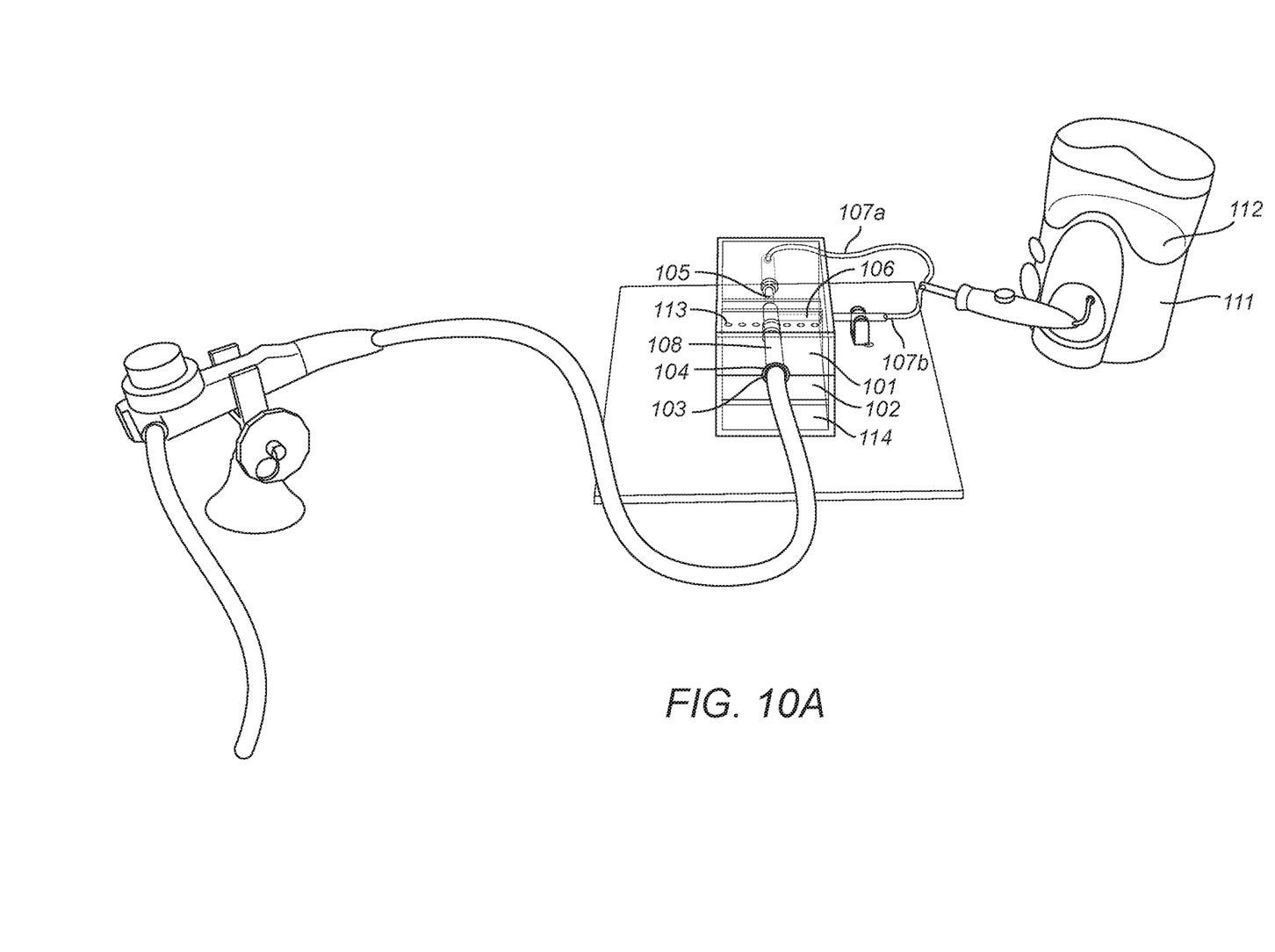
FIGS. 10A-10C illustrate, in accordance with various embodiments of the present invention, one non-limiting example of cleaning devices described herein.
Figure 10B:
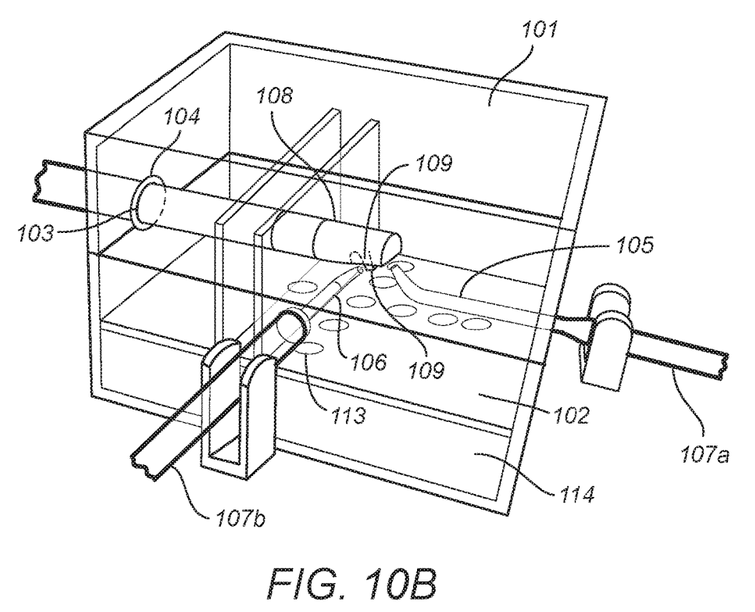
Figure 10C:
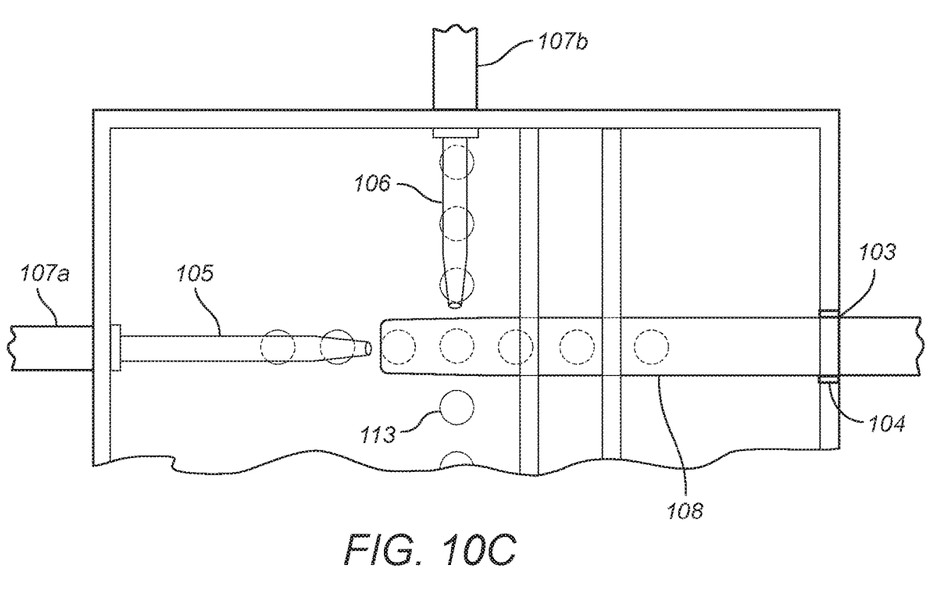

FIGS. 10A-10C illustrate another non-limiting example of the present invention. FIG. 10A provides a three-dimensional view of the system: an endoscope on the left, a cleaning device in the center, and a solution-supplying component on the right including a solution reservoir, a water pump 111 and a magnetic water generator 112. FIG. 10A provides a three-dimensional of the cleaning device. FIG. 10C provides a top view of the cleaning device.

The cleaning device comprises a top cover 101 and a bottom container 102. The top cover and the bottom container can close onto each other to optionally form a water tight seal along their edges, and may include one opening 103 on the side. The opening 103 on the side may comprise a water seal rim 104 along its periphery. The bottom container comprises nozzle 105 and nozzle 106, which are in fluid communication with tubes 107a and 107b. The two nozzles 105 and 106 are configured to match or otherwise accommodate the space geometry surrounding an elevator of endoscopes (e.g., duodenoscopes, linear echoendoscopes, side viewing endoscopes, and other endoscopes with an elevator mechanism). As a result, the two nozzles 105 and 106 can be positioned close to and/or inserted, to independently varying angles and/or depths, into the recesses surrounding an elevator 109 on an endoscope tip 108.

The endoscope cleaning device can also comprise drainage holes 113 on the bottom of the bottom container 102. A drainage collection component 114 can be placed under the endoscope cleaning device for collecting the liquid and debris drained from the endoscope cleaning device. The drainage collection component 114 and the bottom container 102 of the endoscope cleaning device can form water and/or air tight seals along the edges where they contact each other. The drainage collection component can be connected to a vacuum for removal of the liquid and debris drained from the endoscope cleaning device.

For cleaning an endoscope tip 108 with an elevator 109 (for example, the tip of a duodenoscope), the endoscope tip 108 is placed into the bottom container through opening 103 on the side, and the two nozzles 105 and 106 are inserted into the recesses surrounding the elevator 109. The top cover 101 is closed onto the bottom container 102. A water tight seal is formed along the edges where the top cover 101 and the bottom container 102 contact each other. The opening 103 on the side encloses the endoscope tip 108 and the water seal rim 104 forms water tight seal around the endoscope tip 108. The tubes 107a and 107b are connected via one or more connecting tubes to various components of the endoscope cleaning system described herein, which may include, but are not limited to, a water pump 111 for supplying high pressure water or solution jets into the endoscope cleaning device; a magnetic water generator 112 for magnetically charging water or other solutions, including but not limited to solutions like anti-infection solutions, anti-septic solutions, foam forming soap solutions, and other disinfectants, supplied into the endoscope cleaning device; an air pump for supplying high pressure air into the endoscope cleaning device; and a vacuum for removing air, water, or other solutions out of the endoscope cleaning device. In this non-limiting example, the water pump 111 and the magnetic water generator 112 are housed together as one unit.

Figure 8A:
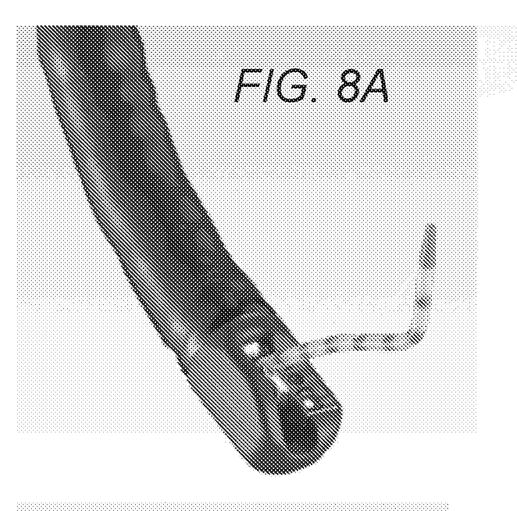
FIGS. 8A-8H (prior art) illustrate, in accordance with various embodiments of the present invention, certain of the medical tools with an elevator mechanism that may be cleaned by various devices contemplated herein. Non-limiting examples of these suitable medical tools include duodenoscopes, linear echoendoscopes, and other endoscopes manufactured by OLYMPUS (FIG. 8B, and FIGS. 8E-H), PENTAX (FIGS. 8C and 8D), FUJIFILM (FIG. 8A) and other manufacturers.
Figure 8B:
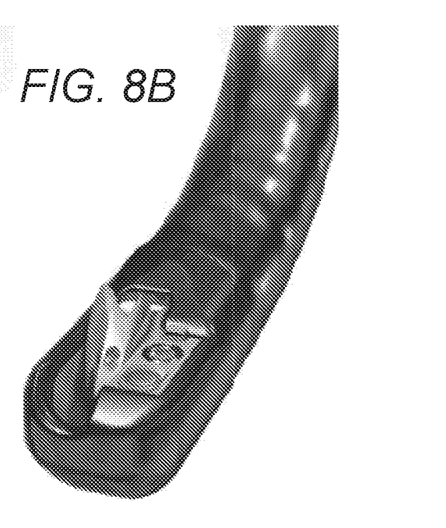
Figure 8C:
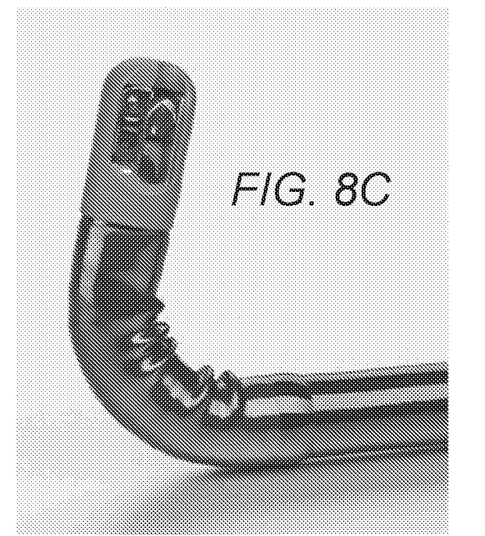
Figure 8D:
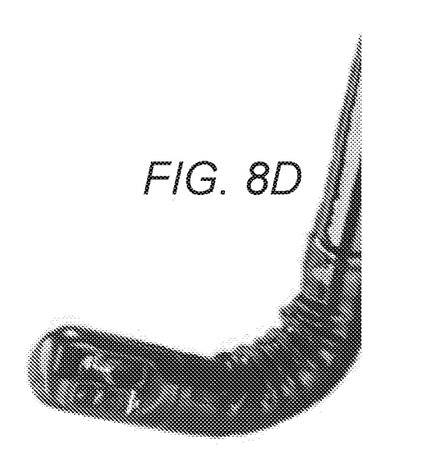
Figure 8E:
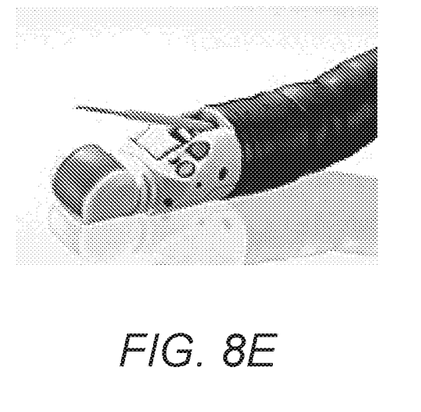
Figure 8F:
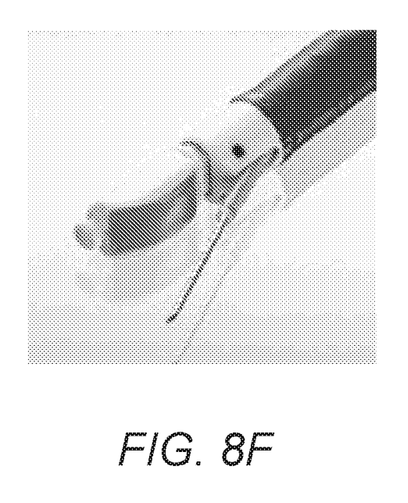
Figure 8G:
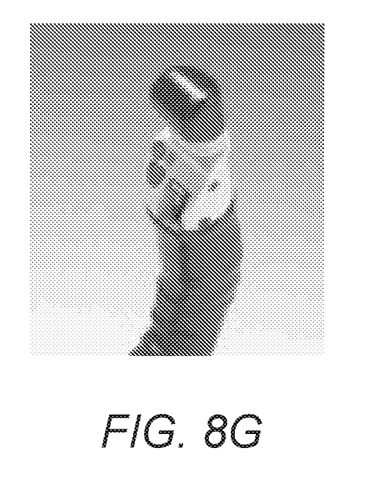
Figure 8H:
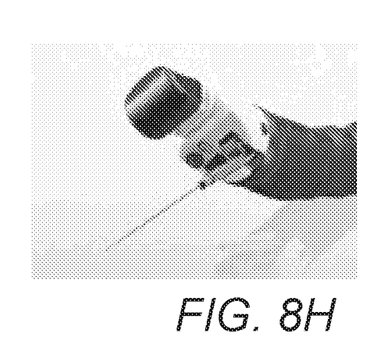

Various medical tools with an elevator mechanism can be cleaned by various devices, systems and methods described herein. Non-limiting examples of these suitable medical tools include duodenoscopes, linear echoendoscopes, and other endoscopes manufactured by OLYMPUS (FIG. 8B, and FIGS. 8E-H), PENTAX (FIGS. 8C and 8D), FUJIFILM (FIG. 8A) and other manufacturers.

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." As one non-limiting example, one of ordinary skill in the art would generally consider a value difference (increase or decrease) no more than 5% to be in the meaning of the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Some types of endoscopes, such as side viewing duodenoscopes and linear echoendoscopes, have an elevator at their tips. Because the narrow crevices and spaces around the elevator are difficult to reach, these medical tools cannot be reliably cleaned. Indeed, the debris and body fluids retained on duodenoscopes have been reported to cause transmission of multi-drug resistant bacteria. To solve the problem, various embodiments of the present invention provide a cleaning device. In some embodiments, the cleaning device is disposable and single use. In other embodiments, the cleaning device is reusable. In various embodiments, the cleaning device has two nozzles arranged in such a way that they can be positioned near and/or inserted into the two spaces beside the elevator. The two nozzles are also connected via tubing to a pump, one or more liquid containers for water and/or disinfectant solutions, and a magnetic water generator that magnetically charges water (and/or disinfectant solutions). The water (and/or disinfectant solutions) that has been magnetically charged is then referred to as "magnetic water" (and/or "magnetic disinfectant solutions"). After the endoscope tip is placed in the tray, the top cover is closed to create a water tight seal. The pump pumps water (and/or disinfectant solutions) out of the two nozzles as high pressure water jets into the narrow crevices and spaces around the elevator, and as a result, any debris and body fluids retained there are cleaned by the water jets' force and magnetic charge. Various cleaning devices and systems described herein can be used for cleaning side viewing duodenoscopes and linear echoendoscopes manufactured by OLYMPUS, PENTAX, FUJIFILM, FUJINON, HOYA, KARL STORZ GmbH & Co., US ENDOSCOPY, BOSTON SCIENTIFIC, MEDTRONIC, and ENDOCHOICE.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of cleaning a tool comprising an elevator mechanism, the method comprising:
   inserting the tool into a device, the device comprising:
      a container including drainage holes in a bottom of the container;
      two nozzles fluidly connected to one or more tubes, the two nozzles being configured so that a pressurized water jet of each of the two nozzles contacts spaces around the elevator mechanism;
      a cover being configured to close onto the container, such that the cover and the container form (i) a first water tight seal along edges where the cover contacts the container and (ii) an opening having a water seal rim, the opening being configured to hold the tool, the water seal rim being configured to form a second water tight seal around the tool;
   holding a handle to position the two nozzles near the spaces around the elevator mechanism; and
   actuating the device to clean the tool.

2. A device for cleaning a tool comprising an elevator mechanism, the device comprising:
   a container including drainage holes in a bottom of the container;
   two nozzles coupled to the container and fluidly connected to one or more tubes, the two nozzles being configured to insert into spaces around the elevator mechanism of the tool, such that a pressurized water jet of each of the two nozzles contacts the spaces around the elevator mechanism;
   a cover configured to close onto the container, such that the cover and the container form (i) a first water tight seal along edges where the cover contacts the container and (ii) an opening having a water seal rim, the opening being configured to hold a portion of the tool, the water seal rim being configured to form a second water tight seal around the portion of the tool; and
   a handle configured to position the two nozzles into the spaces around the elevator mechanism.

3. The device of claim 2, wherein the device comprises one tube fluidly connected to the two nozzles.

4. The device of claim 2, wherein the device comprises two tubes fluidly connected to the two nozzles.

5. The device of claim 2, wherein the tool is a duodenoscope, a linear echoendoscope, or a side viewing endoscope.

6. The device of claim 2, wherein the two nozzles are configured to insert into recesses surrounding the elevator mechanism of the tool.

7. The device of claim 2, wherein the portion of the tool is a tip of the tool.

8. A system for cleaning a tool comprising an elevator mechanism, the system comprising:
   a device, comprising:
      a container including drainage holes in bottom of the container;
      two nozzles fluidly connected to one or more tubes, the two nozzles being configured to position near the elevator mechanism of the tool so that a pressurized water jet of the two nozzles contacts the elevator mechanism;
      a cover configured to close onto the container, such that the cover and the container form (i) a first water tight seal along edges where the cover contacts the container and (ii) an opening having a water seal rim, the opening being configured to hold the tool, the water seal rim being configured to form a second water tight seal around the tool; and
      a handle configured to position the two nozzles near the elevator mechanism; and
   a pump configured to supply a liquid into the device, wherein the pump is connected to the device through the one or more tubes.

9. The system of claim 8, wherein the liquid is water, magnetically charged water, a water-based solution, or a magnetically charged water-based solution.

10. The system of claim 8, wherein the liquid is a disinfectant solution.

11. The system of claim 8, wherein the pump is a high pressure pump.

12. The system of claim 8, wherein the pump is configured to pressurize the liquid to about 40-200 PSI.

13. The system of claim 8, further comprising a magnetic water generator configured to magnetically charge the liquid, wherein the magnetic water generator is connected to the pump through the one or more tubes.

14. The system of claim 8, further comprising a vacuum configured to remove air or liquid out of the device, wherein the vacuum is connected to the device through the one or more tubes.

15. The system of claim 8, further comprising a tool comprising an elevator mechanism.

16. The system of claim 15, wherein the tool is a duodenoscope, a linear echoendoscope, or a side viewing endoscope.

17. The system of claim 8, further comprising a drainage collection component, wherein the drainage collection component is configured to receive the bottom of the device and collecting the liquid drained through the drainage holes.

18. The system of claim 17, wherein the drainage collection component and the bottom of the device are configured to form an air tight seal along the edges where the drainage collection component contacts the bottom of the device.

19. The system of claim 17, further comprising a vacuum connected to the drainage collection component and configured to remove air or liquid out of the drainage collection component.

* * * * *